(12) United States Patent
Lynn et al.

(10) Patent No.: US 10,612,275 B2
(45) Date of Patent: Apr. 7, 2020

(54) DUAL-USE RECEPTACLE DOOR LATCH

(71) Applicants: John W. Lynn, Pomona, NY (US); Therese Valdez, Pomona, NY (US)

(72) Inventors: John W. Lynn, Pomona, NY (US); Therese Valdez, Pomona, NY (US)

( * ) Notice: Subject to any disclaimer, the term of this patent is extended or adjusted under 35 U.S.C. 154(b) by 0 days.

(21) Appl. No.: 16/008,545

(22) Filed: Jun. 14, 2018

(65) Prior Publication Data

US 2018/0363331 A1 Dec. 20, 2018

Related U.S. Application Data

(60) Provisional application No. 62/520,679, filed on Jun. 16, 2017.

(51) Int. Cl.

| | |
|---|---|
| *E05B 67/38* | (2006.01) |
| *E05B 17/22* | (2006.01) |
| *E05B 55/00* | (2006.01) |
| *A45C 11/00* | (2006.01) |
| *E05C 1/04* | (2006.01) |
| *E05B 65/00* | (2006.01) |
| *E05B 15/12* | (2006.01) |
| *A45C 13/02* | (2006.01) |

(52) U.S. Cl.
CPC .............. *E05B 67/38* (2013.01); *A45C 11/00* (2013.01); *A45C 11/008* (2013.01);
(Continued)

(58) Field of Classification Search
CPC ... E05C 1/004; E05C 1/04; E05B 9/00; E05B 13/00; E05B 13/001; E05B 17/00;
(Continued)

(56) References Cited

U.S. PATENT DOCUMENTS 2,627,434 A * 2/1953 Woodward .............. E05C 3/047
292/198
5,603,184 A * 2/1997 Campbell ............... E05B 15/10
292/145

(Continued)

FOREIGN PATENT DOCUMENTS

CN 101779862 A * 7/2010
CN 201563974 U * 9/2010
(Continued)

OTHER PUBLICATIONS

Machine translation of CN 203145582, 2019, pp. 1-7 (Year: 2019).*
Machine translation of DE 20216100433, 6 pages (Year: 2019).*

*Primary Examiner* — Christine M Mills
(74) *Attorney, Agent, or Firm* — Malin Haley DiMaggio & Bowen, P.A.

(57) ABSTRACT

A receptacle that can receive a cell phone or other mobile communication device or other useful objects such as keys that attaches over a restroom or changing room door latch used to secure the door during use of the restroom or changing room. Receptacle's position such that the usual insert a cell phone into the receptacle when the restroom stall door is secured closed and locked by a latch bolt. The user will not forget the cell phone because it will be necessary to remove the cell phone to access the latch bolt for unlocking the stall door. The device can also include advertising with DC and disposed on the receptacle surface or adjacent a portion of the receptacle surface. An ultraviolet light can be activated to help as a disinfectant device to kill bacteria and viruses on any cell phones or other objects in the receptacle.

3 Claims, 5 Drawing Sheets

(52) U.S. Cl.
CPC .......... *E05B 17/2023* (2013.01); *E05B 17/22* (2013.01); *E05B 55/00* (2013.01); *E05B 65/0035* (2013.01); *E05C 1/04* (2013.01); *A45C 13/023* (2013.01); *A45C 2011/002* (2013.01); *A45C 2011/003* (2013.01)

(58) Field of Classification Search
CPC ...... E05B 17/22; E05B 65/0035; E05B 67/38; E05B 55/00; A45C 11/008; A45C 2011/002; Y10T 292/096; Y10T 292/03; Y10T 292/1014; Y10T 292/1022; Y10T 292/62; Y10S 292/02; Y10S 292/54; Y10S 292/63; Y10S 292/64
USPC .............. 292/137, 1, 138, 145, 337, DIG. 2, 292/DIG. 54, DIG. 63, DIG. 64
See application file for complete search history.

(56) References Cited

U.S. PATENT DOCUMENTS

| | | | | |
|---|---|---|---|---|
| 5,984,386 | A * | 11/1999 | Clemens | E05C 19/18 292/162 |
| 6,477,872 | B1 * | 11/2002 | Denton, Jr. | E05B 67/36 70/100 |
| 9,624,702 | B1 * | 4/2017 | Faulkner | E05C 19/184 |
| 2015/0233146 | A1 * | 8/2015 | Klevens | E05B 41/00 340/687 |
| 2018/0142497 | A1 * | 5/2018 | Hung | E05B 65/00 |

FOREIGN PATENT DOCUMENTS

| | | | | | |
|---|---|---|---|---|---|
| CN | 202313100 | U | * | 7/2012 | |
| CN | 202338140 | U | * | 7/2012 | |
| CN | 203145582 | U | * | 8/2013 | |
| CN | 203247948 | U | * | 10/2013 | |
| CN | 203424855 | U | * | 2/2014 | |
| CN | 203594270 | U | * | 5/2014 | |
| CN | 105507684 | A | * | 4/2016 | |
| CN | 205548254 | U | * | 9/2016 | |
| CN | 205778011 | U | * | 12/2016 | |
| CN | 107217914 | A | * | 9/2017 | |
| CN | 206801405 | U | * | 12/2017 | |
| CN | 207033071 | U | * | 2/2018 | |
| DE | 202016100433 | U1 | * | 2/2016 | ............. H04M 1/04 |
| GB | 2556912 | A | * | 6/2018 | |
| JP | 2006028900 | A | * | 2/2006 | |
| KR | 101763080 | B1 | * | 7/2017 | |

* cited by examiner

DUAL-USE RECEPTACLE DOOR LATCH

CROSS REFERENCE TO RELATED APPLICATIONS

This application claims the benefit of provisional U.S. Patent Application Ser. No. 62/520,679, filed on Jun. 16, 2017.

BACKGROUND OF THE INVENTION

1. Field of the Invention

This invention relates generally to a restroom or changing room door latch that also includes a container for holding an object such as a mobile phone, and specifically to a restroom stall door sliding bolt latch that is integrated with a mobile phone container.

2. Description of Related Art

It is a common occurrence that a person using a public facility such as a public restroom stall or changing room, has a need to place personal valuable(s), such as a cellphone, in a secure location during use of the facility. Placing the item(s) on a floor of the facility or balancing the item(s) on—e.g., a toilet paper dispenser, can result in the item(s) being damaged and/or forgotten.

Therefore, it would be desirable to provide apparatus and methods for safely storing valuables, such as a cellphone during the use of a rest room or changing room. It would further be desirable to provide the apparatus and methods in a configuration that also latches a door, such as a door to a changing room or a public restroom stall. It would further be desirable to provide apparatus and methods for reminding a user of the whereabouts of the valuables such as a cell phone prior to the user's departure through the door when sliding the bolt open.

SUMMARY OF THE INVENTION

Apparatus and methods are provided for safely storing valuables, such as a cellphone. The apparatus and methods are provided in a configuration suitable for locking a door, such as a door to a public restroom or changing room stall. Apparatus and methods are also provided for reminding a user of the whereabouts of the valuables prior to the user's departure through the door.

The apparatus may include, and the methods may involve, a latch or lock device for releasably securing a door. The securing of the door may include securing of the door to a building structure. The building structure may include a door jamb. The building structure may include a doorframe. The building structure may include a doorpost. The building structure may include a wall. The building structure may include a second door. The securing of the door may include fixing a position of the door with respect to the building structure. The securing may include latching. The securing may include bolting. The securing may include locking.

The door may include a door of a stall. The stall may include a bathroom stall. The door may include a door of any room, stall or chamber in which a user may wish to store one or more valuables, as well as to be reminded about the whereabouts of the stored valuables prior to leaving the room. Any room, stall or chamber may include a changing room. Any room, stall or chamber may include a capsule hotel "room". Any room, stall or chamber may include a sleep pod.

The device may include a latching member. The latching member may be configured to perform the securing of the door. The latching member may include a bolt. The latching member may feature any suitable geometry for performing the securing. Any suitable geometry may include a chain. Any suitable geometry may include a hook. The latching member may be movable. The latching member may be slidable. The latching member may be slidable in a channel. The channel may be defined by a latching member guide. The guide may include one or more guide walls. The guide walls may include interior guide wall surfaces conforming to an external geometry of the latching member. Alternatively and/or additionally, the latching member may swing on a hinge. The bolt may include a rod. The bolt may include a bar. The bolt may include a shaft. The bolt may include a panel. The latching member may include any suitable material, such as metal and/or a polymer. The latching member may be of a suitable stiffness to prevent manual deflection thereof.

The device may include a valuables-storing member. The device may include a back plate. The latching member may be assembled to the back plate. The valuables-storing member may include the back plate.

The valuables-storing member may be configured to receive the one or more valuables. The valuables-storing member may be configured to store the one or more valuables. The valuables may include one or more than one cellphone. The valuables may include one or more than one smartphone. The valuables may include one or more than one PDA device. The valuables may include one or more than one tablet. The valuables may include one or more than one laptop. The valuables may include one or more writing implements. The valuables may include one or more keys and/or key rings. The valuables may include one or more than one wallet. The valuables may include one or more than one garment and/or accessories. The garment may include outerwear such as a coat, jacket, sweater, glove, hat or scarf. The garment may include a shirt, blouse, skirt or pants. The garment may include an undergarment. The accessories may include sunglasses, cufflinks, jewelry and/or a watch. The valuables may include one or more than one bag. The bag may include a handbag. The bag may include a briefcase. The bag may include a backpack. The bag may include a shopping bag. The bag may include a purse. The valuables may include any item(s) a user may desire to store in the valuables-storing member.

The valuables-storing member may be configured to receive, store, secure, carry, hold and/or contain the valuables therein and/or thereon. The valuables-storing member may be of a suitable material to store, secure, carry, hold and/or contain the valuables therein and/or thereon. Suitable material may include metal and/or a polymer. The valuables-storing member may be of a suitable geometry to receive, store, secure, carry, hold and/or contain the valuables therein and/or thereon.

For example, the valuables may include a smartphone, such as the APPLE™ iPhone™ 7, having dimensions of about 138 mm×about 67 mm×about 7 mm. The suitable geometry for embodiments of the valuables-storing member may include a geometry slightly larger than about 138 mm×about 67 mm, i.e., in order to accommodate the smartphone in a first orientation. The suitable geometry for embodiments of the valuables-storing member may include a geometry slightly larger than about 67 mm×about 7 mm, i.e., in order to accommodate the smartphone in a second orientation. The suitable geometry for embodiments of the valuables-storing member may include a geometry slightly larger than about 138 mm×about 7 mm, i.e., in order to accommodate the smartphone in a third orientation.

The valuables-storing member may be configured to include the latching member. The valuables-storing member may be configured to receive the latching member. The valuables-storing member may be configured to movably receive and/or movably hold the latching member. The valuables-storing member may be configured to slidably receive and/or slidably hold the latching member. The latching member may be configured to move within the valuables-storing member. The latching member may be configured to move along a side of the valuables-storing member. The latching member may be configured to move within a portion of the valuables-storing member. The portion may include the channel. The latching member may be configured to slide within the valuables-storing member. The latching member may be configured to slide within the portion of the valuables-storing member. The latching member may be configured to move with respect to the valuables-storing member. Alternatively and/or additionally, the latching member may be configured to move together with the valuables-storing member.

The valuables-storing member may include one or more than one track. The portion of the valuables-storing member may include the one or more than one track. The bolt may include one or more than one boss. The boss may include any suitably shaped projection. Any suitably shaped projection may include a knob and/or a tab. The boss may be configured to slidably engage the track. Alternatively and/or additionally, the bolt may include the track and the valuables-storing member may include the boss configured to slidably engage the track. Engagement of the boss with the track may prevent the latching member from being slid beyond an optimal position. The engagement may prevent the bolt from being slid out of the channel.

The valuables-storing member may include a receptacle. The valuables-storing member may define a receptacle. The receptacle may include a pocket. The receptacle may include a pouch. The receptacle may include a container. The receptacle may include a box. The receptacle may be configured to receive, carry, secure and/or hold the valuables. The receptacle may be of a size, geometry and/or material suitable for receiving, carrying, securing and/or holding the valuables therein and/or thereon. For example, the receptacle geometry may include a geometry, for embodiments of the receptacle, slightly larger than about 138 mm×about 67 mm, i.e., in order to accommodate the smartphone in a first orientation. The receptacle geometry, for embodiments of the receptacle, may include a geometry slightly larger than about 67 mm×about 7 mm, i.e., in order to accommodate the smartphone in a second orientation. The receptacle geometry may include a geometry, for embodiments of the receptacle, slightly larger than about 138 mm×about 7 mm, i.e., in order to accommodate the smartphone in a third orientation.

The valuables-storing member may include one or more than one hook. The hook may include a peg. The hook may include a knob. The hook may include any size, geometry and material suitable for hanging the valuables thereon. Any suitable geometry may include a clip. The hook may be configured to accommodate the valuables.

The apparatus may involve, and the methods may include, installation of the device onto a building structure. The structure may include the door. The structure may include the wall. The structure may include the jamb. The structure may include the doorframe. The structure may include the doorpost.

The valuables-storing member may include one or more recesses. The recesses may be configured for fixing hardware there through. The hardware may include threaded hardware, such as one or more machine screws. The hardware may be fixed through the recesses to the building structure.

The installation may include fixing one or more parts of the device to the structure. The parts may include the back plate. The installation may include fixing the hardware to the structure. The installation may include fixing the hardware through the back plate to the structure. The installation may include fixing the hardware through the recesses to the structure. Fasteners such as screws, bolts, and nails may be used. The installation may include any suitable fixing. Any suitable fixing may include adhesion with an adhesive. Any suitable fixing may include welding.

The device may include one or more spacers. The back plate may include the spacers. The spacers may perform an optimization of a positioning of the device upon installation of the device to the building structure. The optimization may include preventing a surface of the structure from interfering with a function of the device. The function of the device may include sliding the latching member to latch and/or unlatch the device. The spacers may include the recesses. The spacers may be configured to accommodate the hardware. The spacers may be configured to accommodate the hardware such that, upon installation of the device with the hardware, the device may be securely held to the building structure.

The device may include one or more access windows. The access windows may be configured for accessing the hardware in the recesses. The access windows may be configured for accessing the hardware to perform the fixing of the hardware.

The device may include a reminder mechanism. The reminder mechanism may be configured to alert the user to prevent the user from forgetting the valuables stored in and/or on the valuables-storing member. The reminder mechanism may include a configuration of the device for providing a view of the valuables. The valuables-storing member may be configured to provide the view. The valuables-storing member may include a viewing window configured to provide the view. The valuables-storing member may include a transparent material to provide the view. The valuables-storing member may include a translucent material to provide the view. The geometry of the valuables-storing member may be configured to provide the view. The view may be configured to alert the user to the presence of the valuables in the valuables-storing member. The view may be configured to remind the user of the presence of the valuables in the valuables-storing member. Alternatively, or additionally, the view may enable utilization of the valuables while the valuables are stored in the valuables-storing member. The utilization may include viewing a display that may be included by the valuables.

The reminder mechanism may include one or more components configured to restrict a movement of the latching member when an item is positioned inside the receptacle. For example, the latching member may include a valuables-engaging tab and the valuables-storing member may include a tab-accommodating opening configured such that the tab catches on the valuables stored in and/or on the valuables-storing member, thereby preventing unlatching of the door while the valuables are in and/or on the valuables-storing member. The tab may protrude through the opening into the valuables-storing member. The tab may protrude through the opening into the receptacle. The tab may be slidable in the opening. In a latched state of the device, a distance between the tab and a facing edge of the valuables, stored within the receptacle and facing the tab, may be less than the distance needed to slide the latching member to an unlatched state. In some embodiments, sliding the tab toward an unlatched direction while the valuables are stored within the receptacle may cause the tab to abut the facing edge thereby preventing the unlatching.

For example, in some embodiments, the valuables-storing member may be configured to hold a smartphone, such as the iPhone™. The device may be of a geometry that prevents the unlatching when the smartphone is stored in the device. The receptacle may include a receptacle-wall. In an unlatched state of the device, the tab may be positioned in the opening at a first distance from the receptacle wall, the first distance less than a dimension of the smartphone, thereby preventing storage of the smartphone in the receptacle. The dimension of the smartphone may include the width of the smartphone,—e.g. about 67 mm. The dimension of the smartphone may include the length of the smartphone,—e.g. 138 mm. Upon latching the device, the distance of the tab from the receptacle wall may be increased to a second distance greater than the first distance and greater than the dimension of the smartphone such that the smartphone may be stored within the receptacle. An attempt to unlatch the device while the smartphone is stored therein would result in the tab abutting the smartphone thereby preventing the unlatching.

Alternatively, or additionally, the tab may include a handle of the latching member. The valuables held within the receptacle may block access to the handle, thereby preventing the unlatching. For example, the receptacle may have a width of slightly larger than about 138 mm or about 67 mm and a depth slightly larger than about 7 mm. The handle may be recessed inside the receptacle such that a device, of length about 138 mm or of width about 67 mm, stored there within, would block access to the handle.

Alternatively and/or additionally, the reminder mechanism may include one or more sensors, such as optic and/or weight sensors, positioned to detect valuables stored in or on the device. The reminder mechanism may be configured to emit a sensible alert, such as a flashing light and/or sound, sensible by the user trying to leave the door when the valuables are still stored in and/or on the device.

The device may be configured to enable the securing of the door from only one side of the door. The one side of the door may include a side facing the interior of the room. Alternatively and/or additionally, the device may be configured to enable access from an exterior of the room. The device may or may not include security features such as a security lock requiring a key or combination to open and/or close.

In some embodiments of the invention, a movable bolt may be configured to perform the securing of the door. The receptacle may be configured to movably receive the bolt. The receptacle may be configured to hold one or more of a wallet, keys and a cellphone.

In some embodiments, the bolt may be configured to perform a releasable latching of the door to the doorframe. The device may include the receptacle. The receptacle may be configured to receive the bolt.

The receptacle may be configured to attach to the door. Fasteners such as screws, bolts and nails may be used as hardware to fasten the latch and receptacle to a stall door. A keeper may be fastened to a door jamb. The receptacle may be configured to attach to the doorframe. The receptacle may be configured to attach to the doorpost. The receptacle may be configured to attach to the wall. The receptacle may be configured to attach to the jamb. The receptacle may be configured to attach fixedly to the door. The receptacle may be configured to attach fixedly to the doorframe. The receptacle may be configured to attach fixedly to the doorpost. The receptacle may be configured to attach fixedly to the wall. The receptacle may be configured to attach fixedly to the jamb.

The apparatus may include, and the methods may involve, a latch kit for releasably securing the door to the jamb, wall, doorpost and/or doorframe. The kit may include the latching device. The device may include the movable bolt. The bolt may include a handle. The handle may be configured for grasping with fingers. The bolt may include a bolt end.

The kit may include a bolt holder. The bolt holder may be configured to receive and secure the bolt end. The bolt holder may be configured to fixedly attach to the door. The bolt holder may be configured to fixedly attach to the doorpost. The bolt holder may be configured to fixedly attach to the doorframe. The bolt holder may be configured to fixedly attach to the jamb. The bolt holder may be configured to fixedly attach to the wall. The bolt holder may include hardware holes for inserting hardware there through. The bolt holder may include a bolt-catching surface configured to receive the bolt. The bolt-catching surface may be configured to prevent the door from being opened when the bolt is inserted into the bolt holder.

Apparatus and methods in accordance with the invention will now be described in connection with the drawings in FIGS. 1-7. The drawings show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods of the invention may involve some or all of the features of the illustrative apparatus and/or some or all of the steps of the illustrative methods. Illustrative embodiments will now be described with reference to the accompanying drawings, which form a part hereof.

The apparatus and methods of the invention will be described in connection with embodiments and features of illustrative devices. The devices will be described now with reference to the drawings. It is to be understood that other embodiments may be utilized and structural, functional and procedural modifications may be made without departing from the scope and spirit of the present invention.

The device can be used as a disinfection device to kill bacteria, viruses and other similar germs on mobile devices. Ultraviolet light is added to the device with a battery pack or other power source attached. The ultraviolet light is activated by the mobile device been placed into the device. He ultraviolet light is activated by a switch.

The device can include a display panel or portions of the receptacle panel for advertising promotion of any kind so that advertising can be attached to the surface of the mobile receptacle, advertising can be embossed into the container or receptacle surface. Or the entire device can be formed into any shape by any business owner for any business purpose for example a soda bottle.

The device can be controlled remotely. And the device can interact with the mobile device through hands-free operation. This device could also be set up in order to charge a mobile device is placed inside the receptacle.

The device can be placed over any existing bathroom stall door lock to allow the use of the existing lot. With this application, the sliding latch bolt will not be attached to the device. The receptacle containing a mobile device will have an opening on allowing easy to access the existing locking mechanism.

In several environments such as construction environments there is portable sanitation available which is basically a single structure with the door and a portable toilet inside the closed housing. Some of this is referred under the trademark of porta potty. The present invention device can be retrofitted to fit existing locks on a portable sanitation unit. For example one a portable sanitation user locks the door, a red/green indicator outside the door indicates that the unit is in use, the doors locked from inside. Attaching the present invention to the existing lock allows the present invention to be used with the existing lock.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

Figure 1:
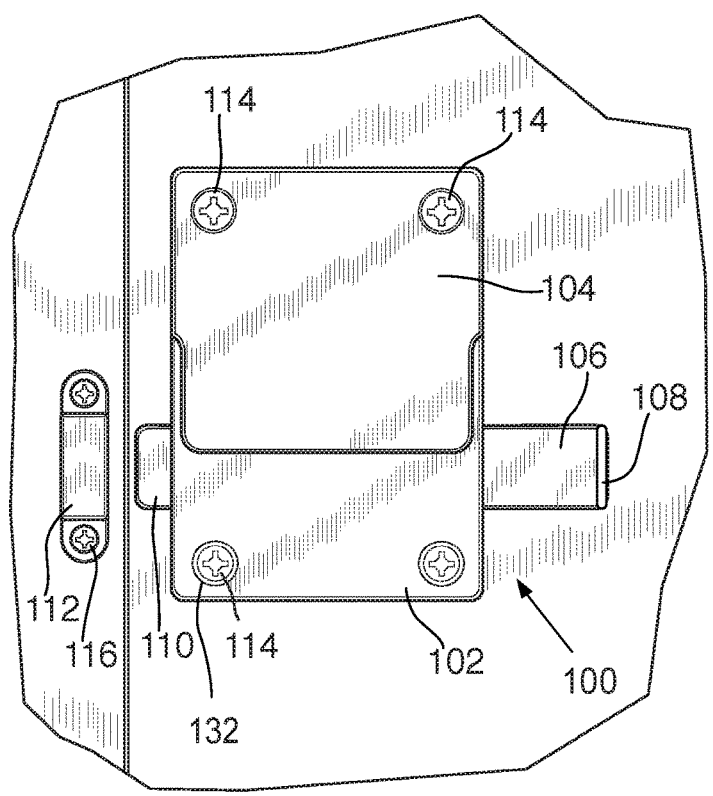
FIG. 1 shows an elevational view of illustrative apparatus in accordance with principles of the invention, the apparatus in a first operational configuration and mounted to a background structure.

FIG. 1 shows latch device 100 in an unlatched state. Latch device 100 includes receptacle 102. Latch device 100 also includes back plate 104. Receptacle 102 may be attached to back plate 104. Receptacle 102 and back plate 104 may adhere to each other. Receptacle 102 and back plate 104 may be of monolithic construction. Latch device 100 includes bolt 106. Bolt 106 includes bolt handle 108 and bolt end 110. Bolt end 110 is shown in a retracted position relative to bolt holder 112. Receptacle 102 may include access windows 132 to aid in fixing of hardware 114 through back plate 104 into a door. Hardware 116 may be fixed through bolt holder 112 into a jamb. Bolt handle 108 can also act as a hook to receive keys, garments, or attach some type of mobile device; or a special adapter can be attached to the bolt handle or other place on the housing to act as a hook for supporting objects.

Figure 2:
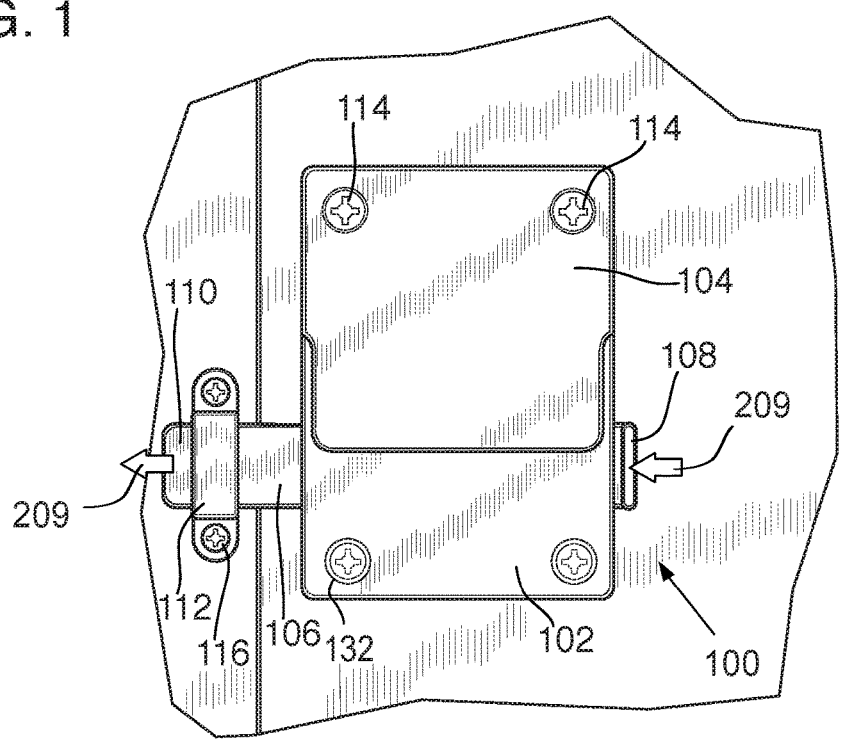
FIG. 2 shows a front elevational view of the apparatus shown in FIG. 1, in which the apparatus is in a second operational configuration.

FIG. 2 shows latch device 100 in a latched state. As indicated by illustrative directional arrows 209, the latched state may be effected by the user having shifted bolt 106 (as shown in FIG. 1) in the direction of arrows 209 by grasping handle 108 and sliding bolt 106 until bolt end 110 is engaged with bolt holder 112. Alternatively, bolt end 110 may be configured for insertion directly into,—e.g., a groove in a thickness of the jamb.

Figure 3:
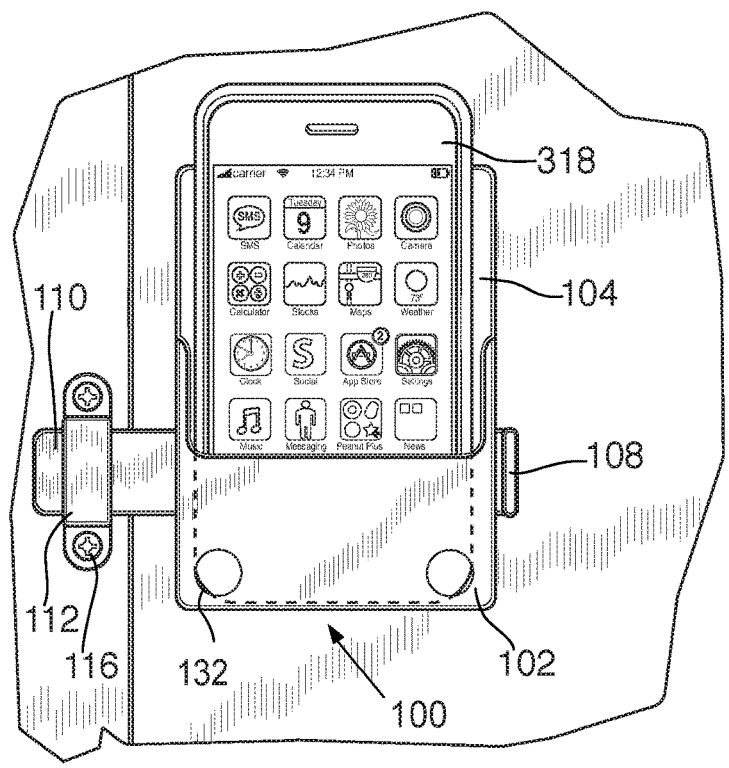
FIG. 3 shows a front elevational view of the apparatus shown in FIG. 1, in which the apparatus is in a third operational configuration, including a workpiece.

FIG. 3 shows latch device 100 in a latched state with cellphone 318 stored in receptacle 102. Receptacle 102 is configured such that cellphone 318 is stored securely there within. Receptacle 102 is further configured such that the user has a view of cellphone 318. The view of cellphone 318 may remind the user to remove cellphone 318 from receptacle 102 prior to exiting the door. In some embodiments, bolt 106 may include a valuables-engaging tab (not shown) extending toward the front of receptacle 102 from a position along bolt 106 between bolt end 110 and the valuables (—e.g., cellphone 318). Receptacle 102 and back plate 104 may define a tab-accommodating opening (not shown) such that, upon the user attempting to unlatch device 100 by sliding bolt 106 opposite to the direction of arrows 209 (shown in FIG. 2), the tab may engage a side of the valuables closer to bolt end 110, thereby preventing unlatching of device 100.

Figure 4:
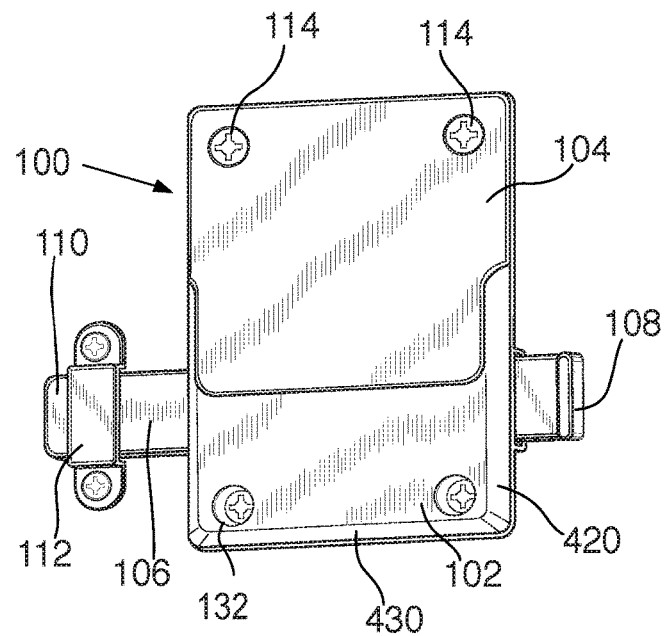
FIG. 4 shows a perspective view of the apparatus shown in FIG. 1, without the background structure.

FIG. 4 shows latch device 100 in a latched state. The perspective view provided shows that receptacle 102 may include sidewalls 420 and bottom wall 430 configured to securely hold one or more valuables therein. Sidewalls 420 and bottom wall 430 may be of a suitable geometry and material to securely store,—e.g., a smartphone (such as cellphone 318 shown in FIG. 3). Alternatively and/or additionally, receptacle 102 may be configured to secure a tablet or other valuables, thereon and/or there within.

Figure 5:
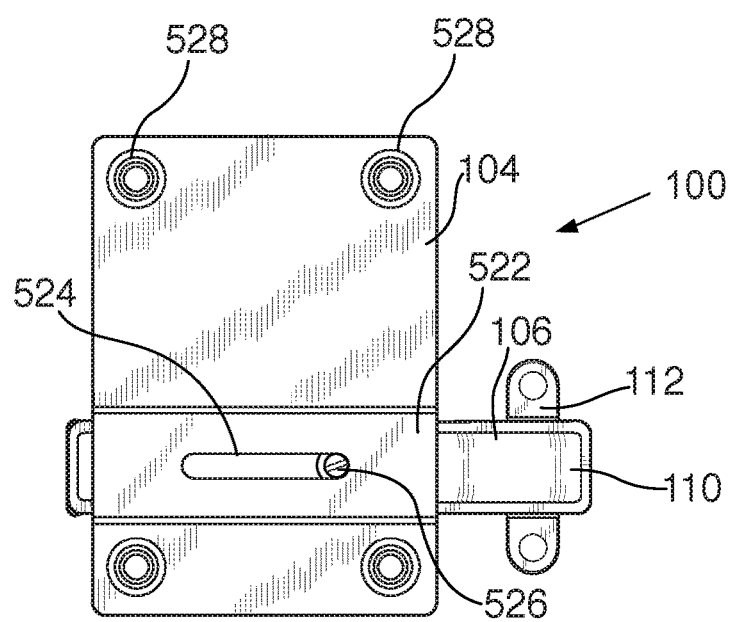
FIG. 5 shows a back elevational view of the apparatus shown in FIG. 1, without the background structure.

FIG. 5 shows a rear view of device 100 in a latched state. Backplate 104 includes spacers 528 which may be configured to accommodate hardware 114 (shown in FIGS. 1, 2 and 4). In the latched state of device 100, bolt end 110 may be positioned athwart a surface of bolt holder 112, thereby securing the door (not shown) in place. Bolt 106 is received within a channel defined by bolt guide 522. Bolt 106 includes boss 526. Bolt guide 522 includes track 524. Boss 526 protrudes into track 524, thereby preventing bolt 106 from extending too far in either a retracted or engaged (latched) direction. Abutment of boss 526 against one end of track 524 may define a limit of the latched state of device 100. Abutment of boss 526 against an opposite end of track 524 may define a limit of the unlatched state of device 100 (shown in FIG. 1).

Figure 6:
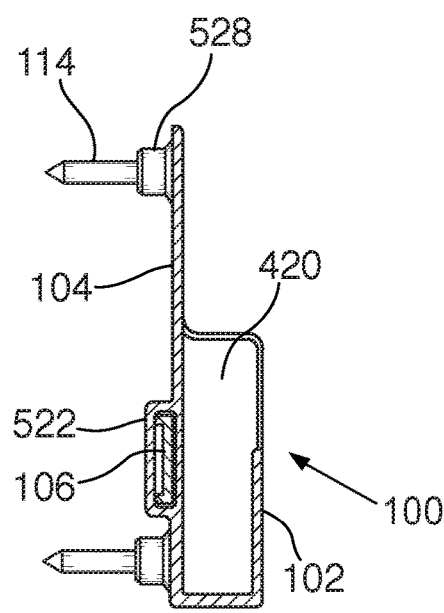
FIG. 6 shows a partial cross-sectional elevational side view of the apparatus shown in FIG. 1, without the background structure.

FIG. 6, featuring a partial cross section of device 100, shows that installation of device 100 may include fixing hardware 114 through recesses in spacers 528 and into the door (not shown). Spacers 528 may be shaped and/or sized to prevent a surface of the door, upon the installation of device 100, from interfering with latching and/or unlatching of bolt 106. Bolt 106 is received within bolt guide 522. Side wall 420 of receptacle 102 may be configured to accommodate,—e.g., cellphone 318 (shown in FIG. 3).

Figure 7:
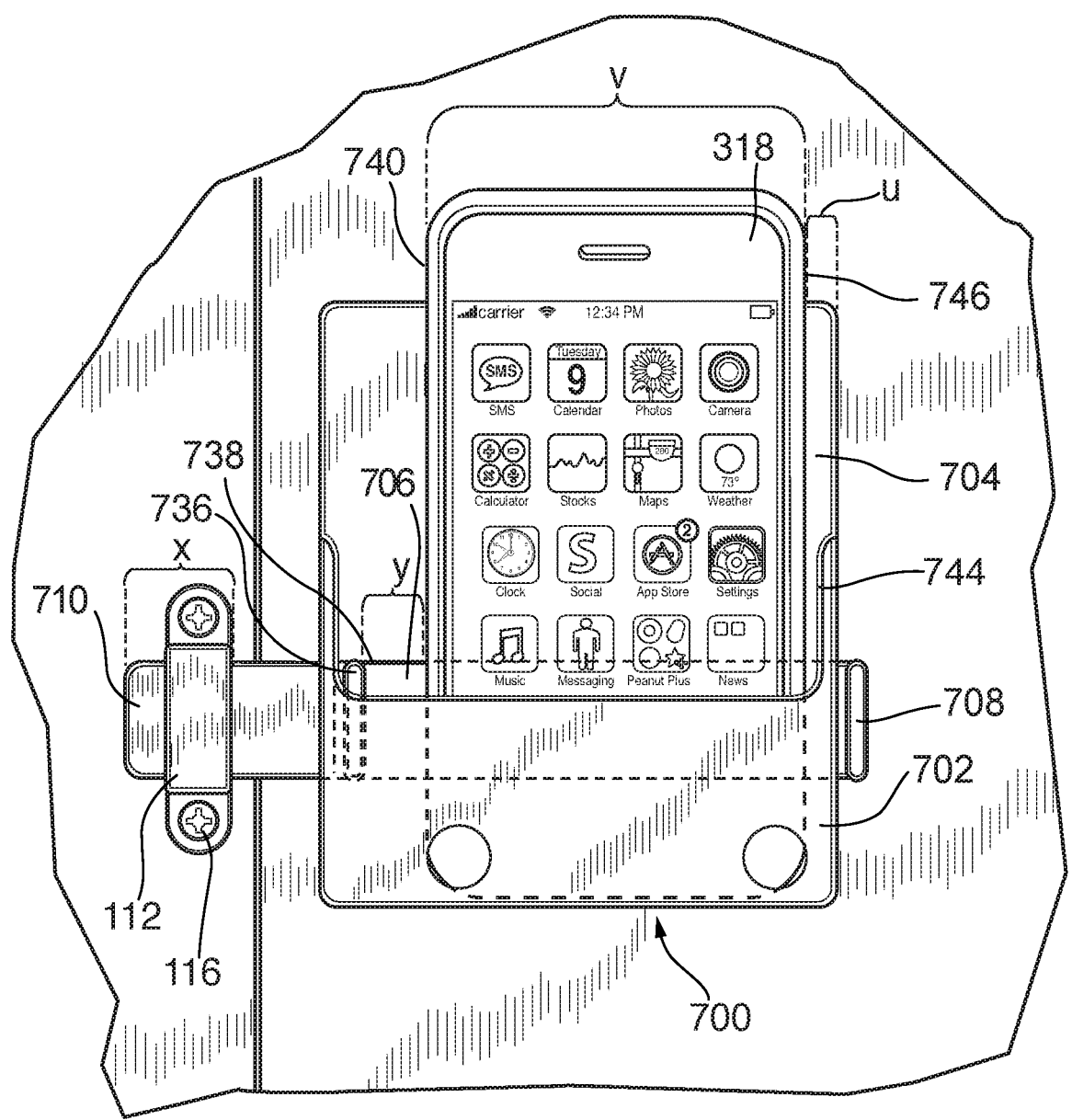
FIG. 7 shows a front elevational view of illustrative apparatus in accordance with principles of the invention, the apparatus mounted to a background structure and including a workpiece.

FIG. 7 shows latch device 700 in a latched state with cellphone 318 stored in receptacle 702, which may include some or all features of receptacle 102 shown in FIG. 1. Receptacle 702 is configured such that cellphone 318 is stored securely there within. Receptacle 702 is further configured such that the user has a view of cellphone 318. The view of cellphone 318 may remind the user to remove cellphone 318 from receptacle 702 prior to exiting the door. Receptacle 702 may include back plate 704, which may include some or all features of back plate 104 shown in FIG. 1.

Latch device 700 may include bolt 706. Bolt 706 may include bolt handle 708 and bolt end 710. Bolt 706, bolt handle 708 and bolt end 710 may, respectively, include some or all features of receptacle bolt 106, bolt handle 108 and bolt end 110, shown in FIG. 1. In some embodiments, back plate 704 may define tab-accommodating opening 738 and bolt 706 may include valuables-engaging tab 736 extending through opening 738 toward the front of receptacle 702.

In the latched state, and with cellphone 318 stored in receptacle 702, tab 736 may be positioned along bolt 706 between bolt end 710 and cellphone 318. Latch device 700 maybe configured such that, in order to unlatch device 700, bolt end 710 must be slid distance x toward receptacle 702, thereby disengaging bolt end 710 from bolt holder 112.

Device 700 may be configured such that, upon the user attempting to unlatch device 700 by sliding bolt 706 away from bolt holder 112, a facing surface of tab 736 may abut cellphone side surface 740 thereby preventing unlatching of device 700. Accordingly, receptacle 702 may be configured such that distance y, between tab 736 and cellphone side surface 740, added to distance u, between opposite cellphone side surface 746 and receptacle inner surface 744, is less than distance x, thereby preventing unlatching of device 700. Accordingly, if cellphone 318 has width v, receptacle 702 may be configured such that, in the latched state, the distance from receptacle inner surface 744 and the facing surface of tab 736 equals u+v+y. Similarly, receptacle 702 may be configured such that, in the unlatched state, the distance from receptacle inner surface 744 and the facing surface of tab 736 is less than v, thereby preventing insertion of cellphone 318 into receptacle 702.

Figure 8:
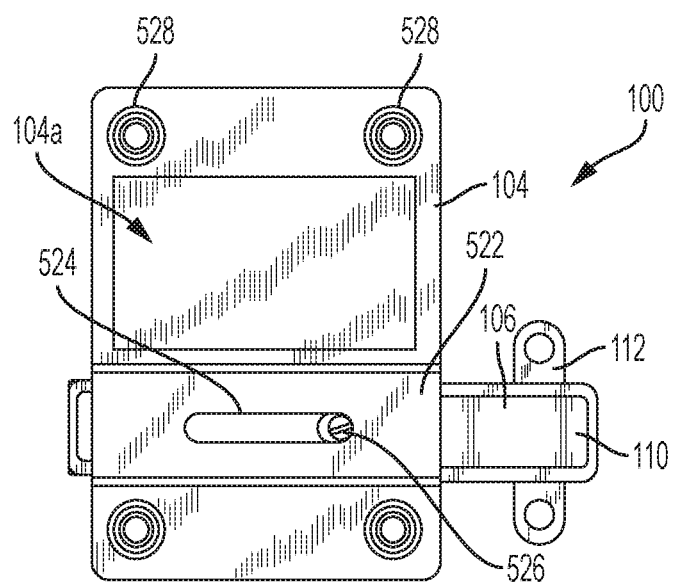
FIG. 8 shows a rear elevational view of an alternate embodiment of the invention which uses an adhesive pad to attach the device to the inside surface of a restroom stall door in lieu of metal fasteners.
Figure 9:
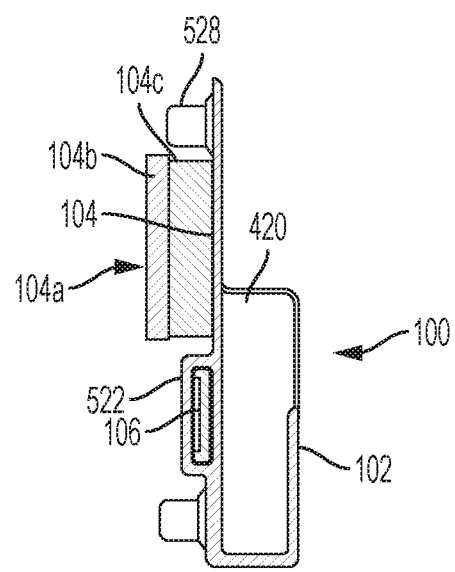
FIG. 9 shows a side elevational view in cross-section of the alternate embodiment using adhesive as shown in FIG. 8.

FIG. 8 and FIG. 9 shows an alternate embodiment of the invention that replaces the hardware screw fasteners with an adhesive pad to attach the device 100 to the inside surface of a restroom or dressing room stall door. FIG. 8 and FIG. 9 show an adhesive pad 104a comprised of a protective cover 104b may be plastic that covers an adhesive surface 104c that is fixed to surface 104 of the device. In use the adhesive plastic cover 104b be removed exposing the adhesive surface 104c which can be compressed against the stall door surface permanently attaching the entire unit 100 to a stall door without using metal screws.

The invention can be used as a disinfection device to kill bacteria, and viruses on mobile devices stored in the receptacle. The ultraviolet light is added to the entire device with the battery pack or other power source attached. The ultraviolet light can be activated by positioning a cell phone or other mobile device being placed into the receptacle. Also the ultraviolet light is activated by a switch.

Thus, apparatus and methods for latching a door, for safely storing valuables and for reminding a user of the whereabouts of the valuables prior to the user's departure through the door, have been provided. Persons skilled in the art will appreciate that the present invention can be practiced by other than the described embodiments, which are presented for purposes of illustration rather than of limitation.

The invention claimed is:

1. A storage device for a mobile communication device, said storage device mountable to a movable closure such as a toilet stall door, said storage device including integrally a door latching device that can be manually activated for locking and unlocking said movable closure comprising:

a box-shaped mobile communication device, storage receptacle having a rectangular back wall sized in vertical length to contact and receive said mobile communication device, a parallel rectangular front wall, smaller in length than said back wall, a pair of vertical rectangular side walls having the same vertical length as said back wall and integrally connected to said back wall and said front wall, and a horizontal rectangular bottom wall integrally connected to said front wall, said back wall and said pair of side walls, said back wall, said front wall, said pair of side walls and said bottom wall forming an open top mobile communication device enclosure sized in width and depth to store said mobile communication device placed therein;

said front wall being approximately half the vertical length of said back wall so that a mobile communication device stored in said enclosure is partially visible when viewing the front of said enclosure;

said back wall having a horizontal, straight top edge and a horizontal straight bottom edge and a horizontal hollow passage, between said back wall top edge and said back wall bottom edge, said hollow passage sized to receive a rectangular, straight, thin toilet stall door latching bolt;

a rectangular thin straight flat latching bolt slidably mounted in said hollow passage, said bolt having a first end and a second end, each first and second end extending horizontally beyond said vertical side walls of said mobile communication device storage receptacle, said second end having a perpendicular tab pointing toward said front wall to allow manual movement of said bolt on one side of said receptacle;

a latch bolt end holder attachable to a toilet door jamb for engaging said first end of said bolt to lock a toilet stall door;

said back wall having at least two apertures to receive threaded fasteners; and means for fastening said back wall to the toilet stall door surface.

2. A storage device as in claim 1 wherein:

said means for fastening includes threaded fasteners for attaching said back wall to the toilet stall door surface; said front wall having at least two apertures sized in diameter to allow a fastening tool head to pass through to manually engage threaded fasteners used to fasten the back wall of said receptacle.

3. A storage device as in claim 1, including:

said means for fastening includes a rectangular pad attached to said back wall having a pad front surface with adhesive for attaching said pad front surface to the toilet stall door flat surface.

* * * * *